(12) United States Patent
Hull

(10) Patent No.: US 7,128,208 B2
(45) Date of Patent: Oct. 31, 2006

(54) PACKAGE FOR STERILE REAMER

(75) Inventor: Les Hull, Attleboro, MA (US)

(73) Assignee: Ethicon, Inc., Somerville, NJ (US)

( * ) Notice: Subject to any disclaimer, the term of this patent is extended or adjusted under 35 U.S.C. 154(b) by 305 days.

(21) Appl. No.: 10/812,246

(22) Filed: Mar. 29, 2004

(65) Prior Publication Data

US 2005/0211595 A1    Sep. 29, 2005

(51) Int. Cl.
A61B 19/02 (2006.01)

(52) U.S. Cl. ............. 206/363; 206/438; 206/523; 53/425; 53/462

(58) Field of Classification Search ........... 206/363, 206/438, 523, 588, 592, 594; 53/425, 462; 229/143, 147, 151, 172, 174
See application file for complete search history.

(56) References Cited

U.S. PATENT DOCUMENTS

| | | | |
|---|---|---|---|
| 2,228,493 A * | 1/1941 | Ilah | 206/214 |
| 3,826,420 A * | 7/1974 | Bamburg et al. | 229/102 |
| 3,937,219 A | 2/1976 | Karakashian | |
| 4,324,331 A | 4/1982 | Ignasiak | |
| 4,524,868 A * | 6/1985 | Buckley et al. | 206/364 |
| 5,356,006 A * | 10/1994 | Alpern et al. | 206/363 |
| 5,447,230 A * | 9/1995 | Gerondale | 206/363 |
| 5,816,403 A | 10/1998 | Wilkes et al. | |
| 2001/0054562 A1 | 12/2001 | Pettersson et al. | |
| 2002/0099382 A1 | 7/2002 | Satazar et al. | |
| 2002/0099383 A1 | 7/2002 | Satazar et al. | |

* cited by examiner

Primary Examiner—David T. Fidei
(74) Attorney, Agent, or Firm—Emil Richard Skula

(57) ABSTRACT

A package for a sterile reamer. The package has an outer foldable package and an inner foam retainer. A sterile surgical instrument in a sealed pouch is contained in the retainer. The package provides economical, protective and space efficient containment for heavy surgical instruments.

5 Claims, 6 Drawing Sheets

PACKAGE FOR STERILE REAMER

TECHNICAL FIELD

The field of art to which this invention pertains is packaging for medical devices, more particularly, packaging for a sterile bone reamer.

BACKGROUND OF THE INVENTION

Packaging for medical devices is well known in the art. The packages may be made from paperboard, polymer films, foils and various combinations. The packaging for sterile medical devices is particularly critical, since the package must not only protect the medical device from damage during shipping and handling, but must also maintain the sterility of the medical device. Any damage to the package that may compromise its integrity as a sterile barrier may result in an unsterile device being used upon or implanted in a patient. This could result in the transmission of infectious agents to the patient during the medical procedure, potentially resulting in, among other things, infection.

Another characteristic of a package for a medical device is the ability to dispense the product in the sterile field without contaminating the sterile field of the operating room. This can be accomplished in a number of ways including the use of multiple layers of sterile packaging, and unfolding of a sterile package in a manner that isolates the sterile interior and contents from the non-sterile exterior of the package.

There is a constant need in this art for novel packages for medical devices having improved characteristics.

SUMMARY OF THE INVENTION

Therefore, a combination package for a heavy surgical instrument such as a sterile reamer is disclosed. The combination package has a folder package. The folder package has a base panel having first and second opposed major sides and first and second opposed minor sides. A front side panel is foldably connected to the base panel along the first major side. The front side panel has opposed ends, and it has a front side end panel foldably attached to each end. A pair of end panels is connected to the minor sides of the base panel. A tab panel is foldably connected to each end panel, each tab panel has a tab member. A tab pocket is located in the base panel adjacent to each end panel. There is a top panel having first and second opposed major sides and opposed minor sides. A rear side panel is foldably connected to the base panel along the second major side of the base panel, and foldably connected to the first major side of the top panel. The rear side panel has opposed ends and a rear end panel is foldably attached to each end. A pair of top end panels is foldably connected to the minor sides of the top panel, and a closure panel is foldably connected to the second major side of the top panel. The combination package has an insert. The insert has a foam member having a central opening for receiving a surgical instrument, and a pair of opposed engagement members projecting into the opening for engaging a section of a surgical instrument. The combination package additionally has a sterile pouch having a top film sealed to a bottom film. The package is used to contain a sterile surgical instrument.

Yet another aspect of the present invention is a method of packaging a sterile surgical instrument using the above described combination package.

These and other aspects and advantages of the present invention will become more apparent from the following description and accompanying drawings.

DETAILED DESCRIPTION OF THE INVENTION

Figure 1:
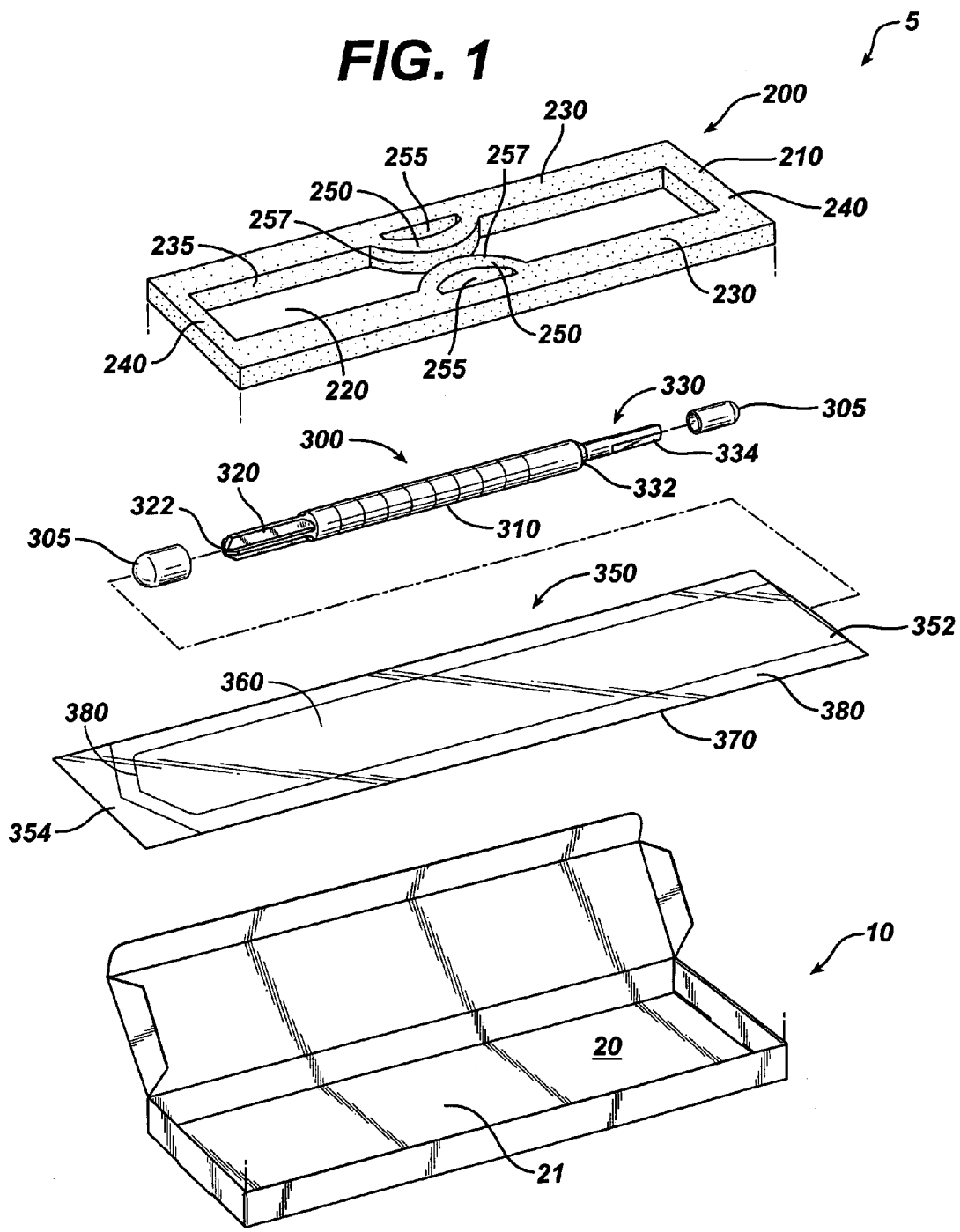
FIG. 1 is an exploded perspective view of a package of the present invention containing a sterile reamer.
Figure 2:
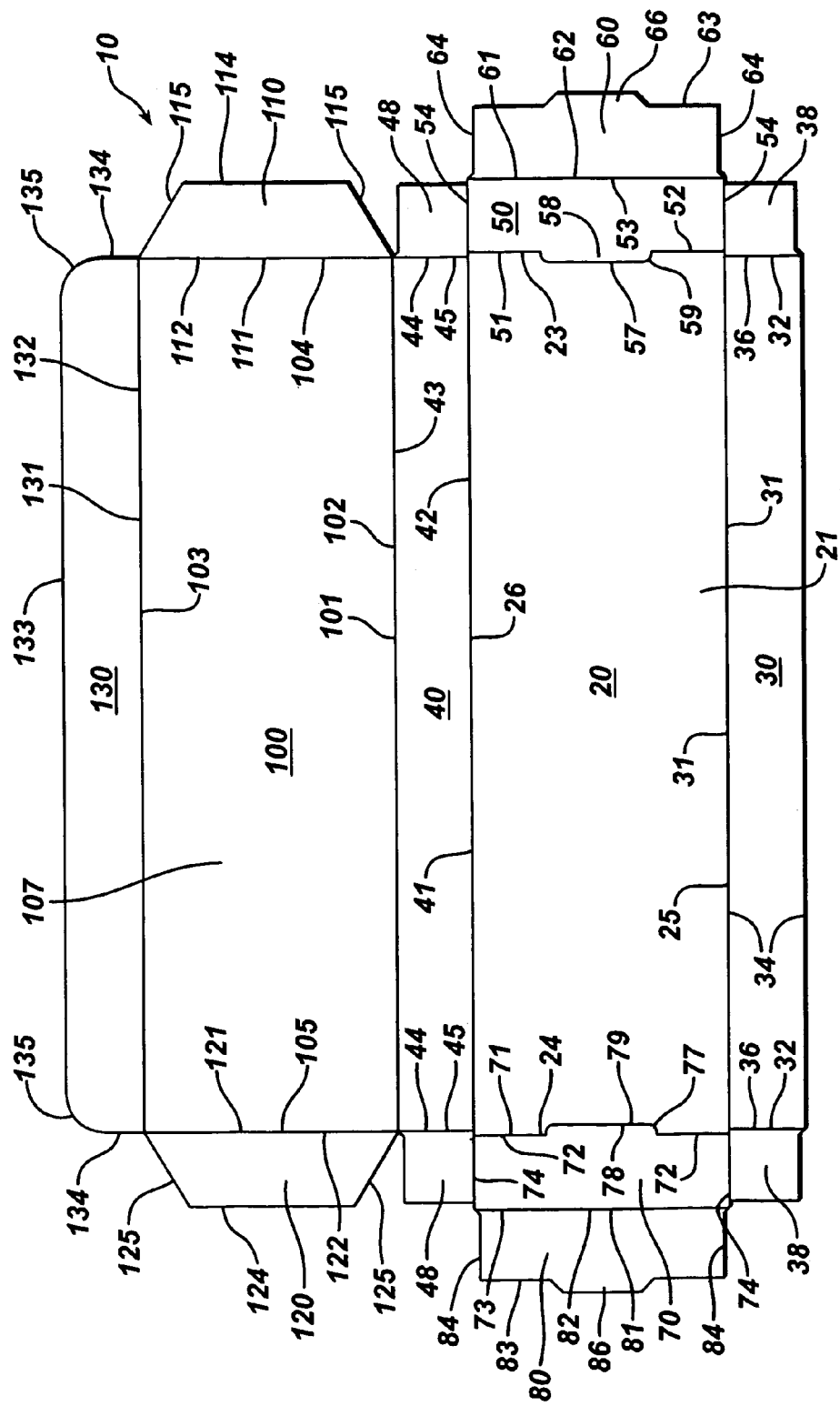
FIG. 2 is a plan view of the novel package of the present invention, prior to folding and assembly.
Figure 3:
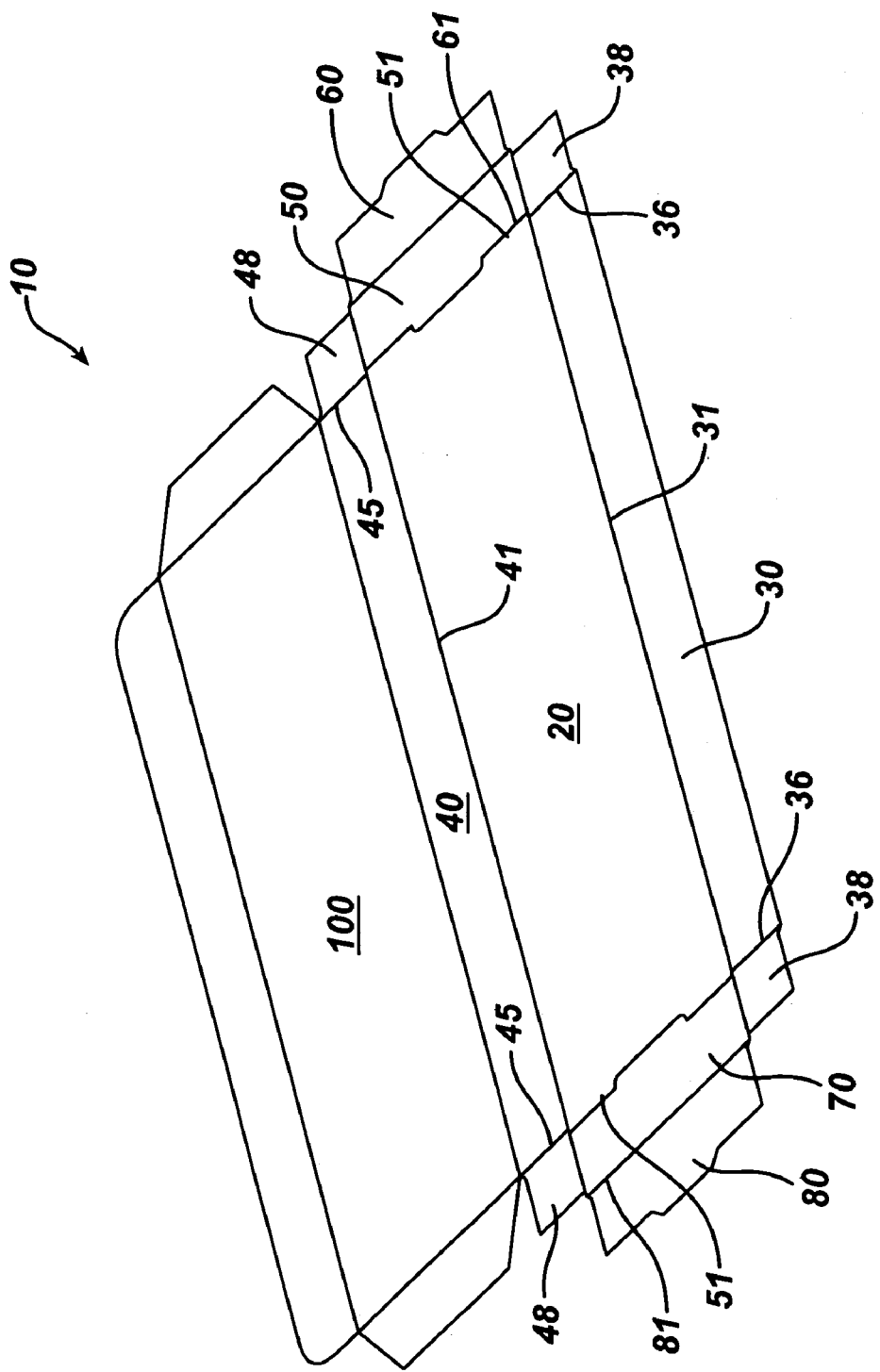
FIG. 3 illustrates the initial step in the sequence of assembly of the package of FIG. 2.
Figure 4:
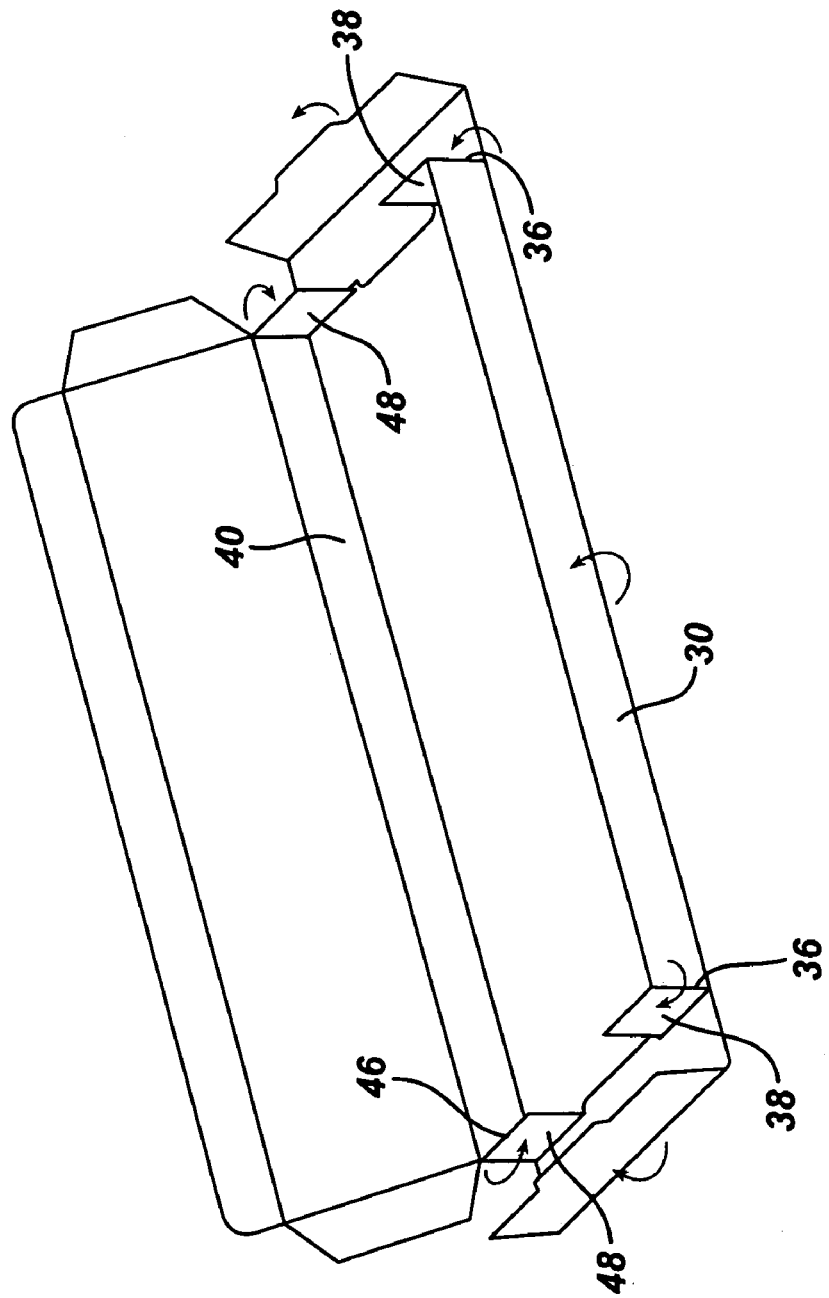
FIG. 4 illustrates the next steps in the sequence of assembly.
Figure 5:
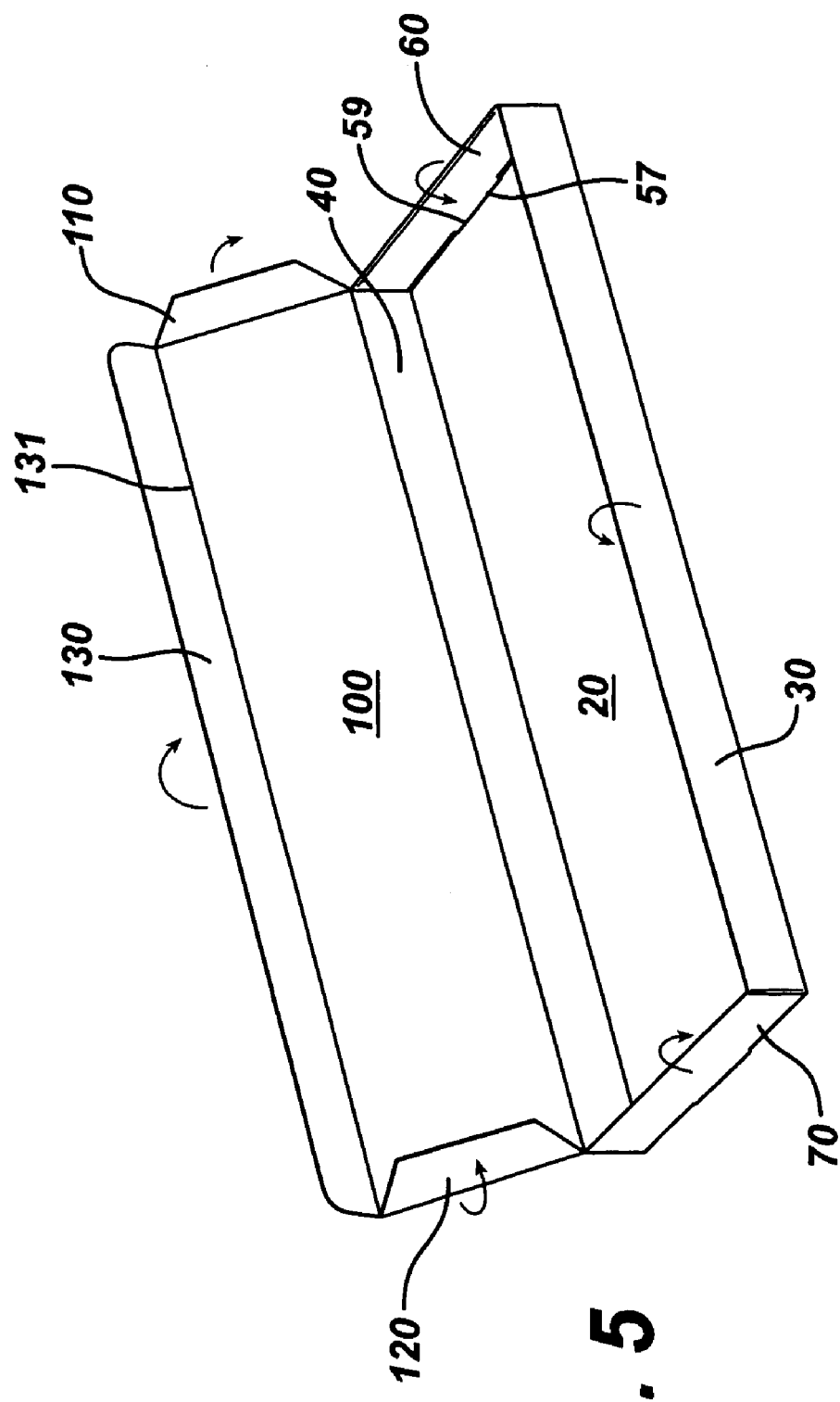
FIG. 5 illustrates the final steps in the assembly of the package prior to inserting the insert and sterile reamer.

Referring to FIG. 1, a package 5 of the present invention is seen to include a foldable package 10. The package 10 is seen to contain the foam protective insert 200. A sterile reamer 300 is seen to be contained in sealed pouch 350 and mounted in package 10 such that it is engaged by insert 200. A plan view of package 10 is illustrated in FIG. 2. The package 10 is seen to have base panel 20 having top 21 and bottom 22. The base panel 20 is seen to have opposed ends 23 and 24, and opposed front side 25 and rear side 26. The front side panel 30 is seen to be foldably connected to base panel 20 along fold line 31. Front side panel 30 is seen to have opposed ends 32 and opposed sides 34. Extending from each end 32 along fold lines 36 are the panels 38. Foldably connected to the ends 23 and 24, respectively, of the base panel 20 are the end panel 50 and the end panel 70. End panel 50 is connected along fold line 51, while end panel 70 is connected along fold line 71. End panel 50 is seen to have opposed major sides 52 and 53 and opposed ends 54. Slit 57 is seen to extend into base panel 20 from side 52 forming tab member 58 and tab pocket 59. Tab panel 60 is seen to be foldably connected to tab panel 50 along fold line 61. Tab panel 60 is seen to have opposed major sides 62 and 63, and opposed ends 64. Tab member 66 is seen to extend outwardly from a central section of side 63. End panel 70 is seen to be foldably connected to base panel 20 along fold line 71 and to have opposed major sides 72 and 73 and opposed ends 74. Slit 77 is seen to extend into base panel 20 from side 72 forming tab member 78 and tab pocket 79. Tab panel 80 is seen to be foldably connected to tab panel 70 along fold line 81. Tab panel 80 is seen to have opposed major sides 82 and 83, and opposed ends 84. Tab member 86 is seen to extend outwardly from a central section of side 83.

Foldably connected to the base panel 20 along fold line 41 is the rear side panel 40. Rear side panel 40 is seen to be substantially rectangularly shaped with a pair of opposed major sides 42 and 43 and a pair of opposed end sides 44. Foldably connected to end sides 44 along fold lines 45 are the extension panels 48. Top panel 100 is seen to be foldably connected to rear side panel 40 along fold line 101. Top panel 100 is seen to be substantially rectangularly shaped with opposed major sides 102 and 103, and opposed minor sides 104 and 105. The panel 100 is also seen to have top 107 and bottom 108. Foldably connected to side 104 of panel 100 along fold line 111 is the top end panel 110. Top end panel 110 is seen to have a substantially trapezoidal shape with first side 112, second opposed side 114, and angulated sides 115. Foldably connected to the opposite side 105 of top panel 100 along fold line 121 is the top end panel 120. Top end panel 120 is seen to have a substantially trapezoidal shape with first side 122, second opposed side 124, and angulated sides 125. The closure panel 130 is seen to be foldably connected to top panel 100 along fold line 131. Closure panel 130 has first longitudinal side 132 and second opposed longitudinal side 133. Closure panel 130 has opposed end sides 134. Panel 130 is seen to have rounded corners 135 at the intersections of the end sides 134 with the longitudinal side 133.

Referring now to FIGS. 1 and 3–6, the package 10 is assembled in the following manner. Rear side panel 40 is rotated about fold line 41 such that it is substantially perpendicular to base panel 20. Extension panels 48 are then rotated inwardly about fold lines 45 such that panels 48 are substantially perpendicular to rear side panel 40. Next, front side panel 30 is rotated about fold line 31 to a position substantially perpendicular to base panel 20. Panels 38 are then folded inwardly about fold lines 36. Preferably next, end panel 50 is rotated upwardly about fold line 51, and end panel 70 is similarly rotated upwardly about fold line 71, such that both panels 50 and 70 are substantially perpendicular to base panel 20. Rotation of panels 50 and 70 results in the opening of slits 57 and 77 to form tab pockets 59 and 79, respectively. Next, tab panel 60 is rotated about fold line 61, and over extension panel 48 and panel 38 such that it is substantially perpendicular to base panel 20 and parallel to end panel 50, and tab member 66 is then engaged in tab pocket 59, thereby locking panels 50 and 60 in place. Next, tab panel 80 is rotated about fold line 81, and over extension panel 48 and panel 38 such that it is substantially perpendicular to base panel 20 and parallel to end panel 70, and tab member 86 is then engaged in tab pocket 79, thereby locking panels 70 and 80 in place. Next, closure panel 130 is rotated about fold line 131 such that it is substantially perpendicular to top panel 100, and, top end panel 110 is rotated about fold line 111 and top end panel 120 is rotated about fold line 121 such that panels 110 and 120 are substantially perpendicular to top panel 100. Finally, top panel 100 is rotated about fold line 101 such that the top panel 100 is substantially parallel to base panel 20, with the top 107 in facing the interior of the package 10 and the bottom 108 is on the exterior. In this assembled configuration, side 133 of closure panel 130 and sides 124 and 114 of top end panels 120 and 110 rest on top 21 of base panel 20.

Figure 6:
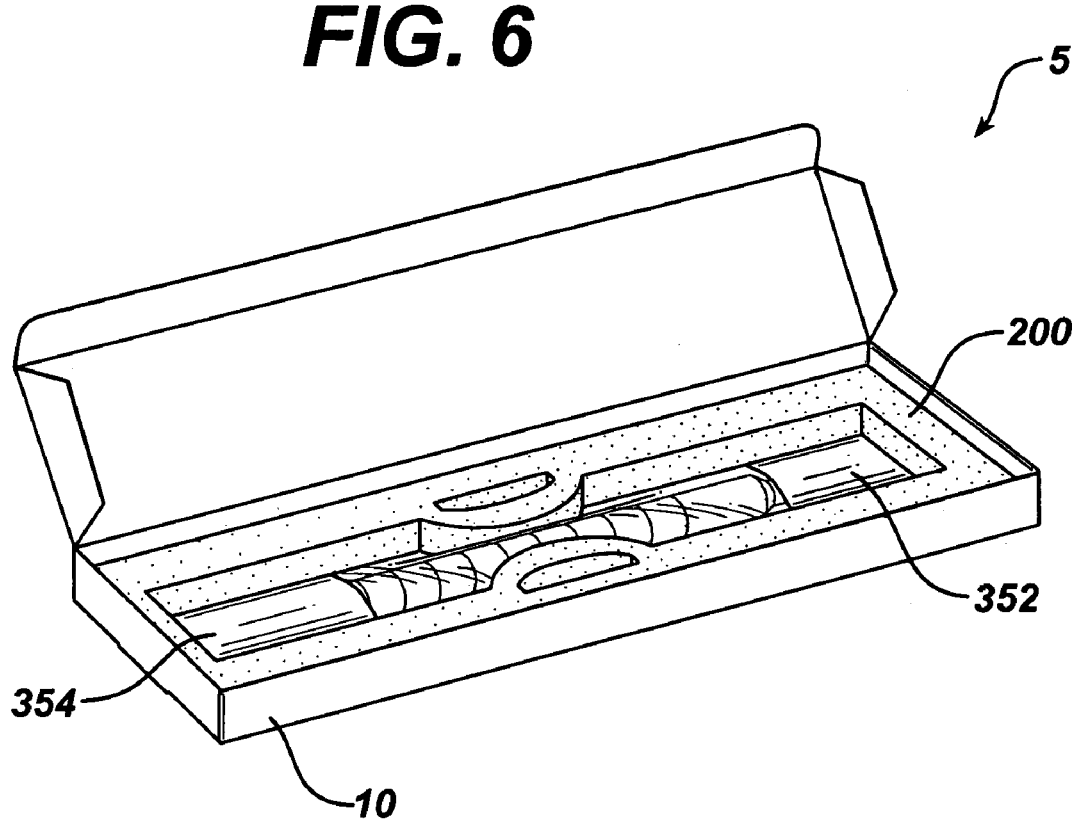
FIG. 6 illustrates the package of the present invention, after the insert has been emplaced and a sterile reamer mounted therein.

An insert 200 useful in the packages 10 of the present invention to form the package 5 of the present invention is seen in FIGS. 1 and 6. The insert 200 is seen to be an elongate member 210. It is preferred that member 210 be rectangularly shaped, however retainer 10 may have any desired geometric configuration, including oval, square, polygonal, etc., and combinations thereof. Member 210 is seen to have inner opening 220 creating opposed longitudinal outer wall members 230 connected to opposed end wall members 240. Wall members 230 are seen to have inner surfaces 235. A pair of opposed reamer engagement members (or ears) 250 is seen to extend centrally out from the inner surfaces 235 of wall members 230. An optional compression opening 255 is seen to be contained in each engagement member 250 partially extending into wall members 230. Engagement members 250 have engagement surfaces 257. It is particularly preferred that the engagement members 250 have an arcuate shape, however members 250 may have other shapes including triangular, rectangular, square, etc.

Sterile reamer 300 is illustrated in FIGS. 1 and 6. The reamer 300 is seen to be contained in a sealed, conventional sterilization pouch 350 made from polymeric films such as Tyvek spin bonded polyethylene with heat sealed coating and polyester coated clear film made from LDPE. The package is not limited to these material and other medical device pouches composed of different conventional materials can be used. The pouch 350 is seen to have top clear film 360 heat sealed to bottom spin bonded polyethylene film 370 along border seal 380. Reamer 300 is seen to have elongated cylindrical member 310 having proximal end 320 and distal end 330. Proximal end 320 is seen to contain flute members 322. Distal end 330 is seen to taper or neck down at tapered section 332, and is also seen to have flute members 334. The protective caps 305 are optionally mounted to each end. The package containing a reamer 300 is sealed and sterilized in a conventional manner using conventional processes.

The package 5 of the present invention containing the sterile reamer 300 is assembled in the following manner. The insert 200 is inserted into the assembled package 10 such that the bottom of the insert 200 is resting upon the top 21 of base panel 20. The sterile reamer 300 contained in sealed pouch 350 is then placed into opening 220 of insert 200 such that the reamer 300 and package 350 are engaged by surfaces 257 of engagement members (or ears) 250, thereby partially compressing members 250 and causing the members 250 to apply a biasing force and retain the reamer 300 in pouch 350 in a substantially spatially fixed location within package 10. Preferably, the ends 352 and 354 are folded over prior to insertion in opening 220. The top panel 100 is then closed as described above to complete the assembly of package 5.

The packages 10 the present invention may be constructed out of any material which is easily die cut and scored, and easily foldable, and which has sufficient strength and integrity to adequately protect the loop and catheter during sterilization, shipping, handling and storage. Such materials include conventional materials such as medical grade paperboard. It is particularly preferred to use a conventional, stiff paperboard having a thickness of about 0.008" to about 0.016". The paperboard, as previously mentioned, is preferably an appropriate medical grade. Other materials, including plastics, foils, and laminates combined with each other or with paper may also be used. The packages 10 are made using conventional equipment such as die cutting presses. The inserts 200 may be made of conventional foam materials such as polyethylene closed cell foam having a sufficiently effective density, and a sufficiently effective thickness to provide effective cushioning (e.g., 4 lb., and 0.5 inches thick). This will vary depending upon the size and weight of the instrument. Other conventional particulate-free polymers foams and equivalents may be used. The inserts are manufactured by conventional processes such as molding and cutting.

It will be appreciated by those skilled in the art that the size of the package 10 and the panels will vary in accordance with the size of the particular sterile device, e.g., sterile reamer device 200. The package 10 and the panels will be of sufficient size to effectively contain a particular surgical device such as reamer 200 illustrated and described herein. In addition the shapes and configurations of each panel may similarly vary. The size of the insert 200 will vary accordingly. It will be appreciated that while it is preferred to package a sterile reamer in the packages 5 of the present invention, other conventional heavy surgical instruments may be packaged as well.

The packages of the present invention have many advantages. The packages provide a simple cost effective package that will securely hold heavy metal instruments. The packaging of heavy metal instruments will challenge it's own packaging when subjected to a ship test (ISTA-1A, International Safe Transit Association). This package is very cost effective, compact and secures the instruments such that the packaging is not compromised during ship testing. Most heavy metal instruments are packaged using large bulky materials or put into blister trays to secure the instruments. Two problems arise from this method, the first problem is the cost of extra materials to pack the instruments and or the use of blister trays. The second problem is when using extra packaging materials or a blister tray is that the resultant box is very large. Most hospitals have limited storage space for instruments and would prefer packaging as small as possible. The present invention secures heavy surgical reamers in a pouch/foam/box combination. The box and the spring loaded foam insert are such that when a pouched reamer is placed in the box, the top opening design of the box along with the size of the foam insert securely holds the reamer in place with little or no movement allowed. The inward facing ear feature on the foam insert acts as a spring load so that one foam insert will accommodate a multiplicity of different size reamers ranging, for example, from 6 mm in diameter to 12 mm in diameter. This invention provides a unique solution in that the package is cost effective, is very compact and a blister tray is not used. This package is not much larger than the instrument itself.

Although this invention has been shown and described with respect to detailed embodiments thereof, it will be understood by those skilled in the art that various changes in form and detail thereof may be made without departing from the spirit and scope of the claimed invention.

I claim:

1. A package for a sterile reamer, comprising:
  A. a foldable package comprising:
    a base panel having first and second opposed major sides and first and second opposed minor sides;
    a front side panel foldably connected to the base panel along the first major side, said front side panel having opposed ends, and said front side panel having a front side end panel foldably attached to each end;
    a pair of end panels connected to the minor sides of the base panel;
    a tab panel foldably connected to each end panel, each tab panel having a tab member;
    a tab pocket in the base panel adjacent to each end panel;
    a top panel having first and second opposed major sides and opposed minor sides;
    a rear side panel foldably connected along the second major side to the base panel, and foldably connected to the first major side of the top panel, said rear side panel having opposed ends and a rear end panel foldably attached to each end;
    a pair of top end panels foldably connected to the minor sides of the top panel; and,
    a closure panel foldably connected to the second major side of the top panel;
  B. an insert comprising a foam member having a central opening for receiving a surgical instrument, and a pair of opposed engagement members projecting into the opening for engaging a section of a surgical instrument, wherein at least one of the opposed engagement members contains an opening therein; and,
  C. a sterile pouch having a top film sealed to a bottom film, wherein the sterile pouch contains a surgical instruement and wherein such instrument comprises a surgical reamer.

2. The package of claim 1 wherein the insert comprises polyethylene foam.

3. A method of packaging a sterile surgical instrument, comprising:
  I. providing a package, comprising:
    A. a foldable package comprising:
      a base panel having first and second opposed major sides and first and second opposed minor sides;
      a front side panel foldably connected to the base panel along the first major side, said front side panel having opposed ends, and said front side panel having a front side end panel foldably attached to each end;
      a pair of end panels connected to the minor sides of the base panel;
      a tab panel foldably connected to each end panel, each tab panel having a tab member;
      a tab pocket in the base panel adjacent to each end panel;
      a top panel having first and second opposed major sides and opposed minor sides;
      a rear side panel foldably connected along the second major side to the base panel, and foldably connected to the first major side of the top panel, said rear side panel having opposed ends and a rear end panel foldably attached to each end;
      a pair of top end panels foldably connected to the minor sides of the top panel; and,
      a closure panel foldably connected to the second major side of the top panel;
    B. an insert comprising a foam member having a central opening for receiving a surgical instrument, and a pair of opposed engagement members projecting into the opening for engaging a section of a surgical instrument; and,
    C. a sterile pouch having a top film sealed to a bottom film;
  II. placing a surgical instrument in the sterile pouch prior to sealing, and sterilizing the instrument in the pouch; and,
  III. placing the insert into the foldable package, and placing the pouch containing the instrument into the opening in the insert such that the instrument and pouch are engaged by the engagement members.

4. The instrument of claim 3, wherein the instrument is a surgical reamer.

5. The method of claim 3, wherein the engagement members have a compression opening.

* * * * *